United States Patent [19]

Kulik et al.

[11] Patent Number: 4,667,657

[45] Date of Patent: May 26, 1987

[54] SURGICAL WOUND RETRACTOR

[75] Inventors: Yaroslav P. Kulik, Blagoveschensk; Ivan I. Shmyrin, Vladivostok; Rustam I. Utyamyshev, Moscow; Marina N. Vyrzhikovskaya, Moscow; Boris A. Smirnov, Moscow, all of U.S.S.R.

[73] Assignee: Institut Blagoveschensky Gosudarstvenny Meditsinsky, Blagoveschensk, U.S.S.R.

[21] Appl. No.: 789,143

[22] Filed: Oct. 18, 1985

[51] Int. Cl.$^4$ .............................................. A61B 17/02
[52] U.S. Cl. ........................................ 128/20; 128/345
[58] Field of Search ............. 128/341, 345, 20, 303 A; 604/107, 108, 109

[56] References Cited

U.S. PATENT DOCUMENTS 3,039,462  6/1962  Walden et al. ...................... 128/345
3,667,474  6/1972  Lapkin et al. ........................ 128/345
3,789,829  2/1974  Hassou ................................. 128/345
4,585,000  4/1986  Hershenson ......................... 128/345

OTHER PUBLICATIONS

Medical Instruments, Apparatuses, Devices and Equipment, catalogue, vol. 2, No. 05-291, Book 2.
Townok catalogue, p. 8, No. HL-5053.

Primary Examiner—Gene Mancene
Assistant Examiner—John G. Weiss
Attorney, Agent, or Firm—Fleit, Jacobson, Cohn & Price

[57] ABSTRACT

A surgical wound retractor including two diverging branches made up of a stationary part and a movable working part hinged thereto. The working parts of both branches have one common guide which embraces them and is rigidly secured on central rods installed on the stationary parts of the branches, while a movable rod disposed between the stationary parts of the branches has one end connected to the diverging device and the other end to the drive of the diverging device.

2 Claims, 3 Drawing Figures

SURGICAL WOUND RETRACTOR

This invention relates to medical equipment and, in particular, to surgical instruments used in reconstruction surgery, in particular, in thoracic surgery, open-heart operations, implantation of artificial valves, valvuloplasty, stenosis dilation, etc.

During heart operations, such as valvuloplasty, stenosis dilation, implantation of artificial valves, the atrium incision has to be dilated to an optimal size so that it can be made use of with minimal trauma to tissues.

Known in the art are instruments used in thoracic surgery to retract and hold the heart during the operation, for example, a heart spatula comprising a handle and a hook (cf., for example, Medical Instruments, Apparatuses, Devices and Equipment, catalogue, book 2, No. 05-291).

But such instruments cannot be used to dilate the atrium wound during open-heart operations and in many other similar instances.

Also known in the art is a hook for retracting the atrium wound, which comprises a handle and a hook, their sizes varying over a wide range (cf., for example, catalogue "Townok" p. 8, No HL-5053).

During an operation performed inside the heart, an incision is made of a size minimal for a particular case. This incision should then be dilated to make maximum use thereof and provide a satisfactory field of vision and convenient access to a valve and other subvalvular structures of the heart. The use of known surgical hooks for dilation of the heart wound involves a succession of instruments having different widths. This can be traumatic to the atrium tissues and unnecessarily prolong the operation.

Also known in the art is a surgical wound retractor comparising two diverging branches, a diverging device, and a curved working part (cf., for example, catalogue "Townok", p. 8, No HL-5042). This known wound retractor is deficient in that, when the surgeon retracts the edges of the wound, his hand obstructs the view to the surgical field. Further manipulations become difficult, considering they are to be made inside the wound, and the operation is prolonged.

SUMMARY OF THE INVENTION

It is the primary object of the invention to ensure uninterrupted dilation of the wound edges with minimal trauma to the atrium tissues.

Another object of the invention is to ensure a good field of vision of the surgical field with the minimal incision of the atrium wall.

One more object of the invention is to provide conditions for swift dilation of the wound edges, making utmost use of the available wound size.

It is an important object of the invention to ensure that the operative field is not obstructed when the wound retractor is installed.

And, finally, it is also an object of the invention to cut down the length of the operation.

These and other objects of the invention are achieved in that in a surgical wound retractor comprising diverging branches featuring curved working parts and provided with a diverging device, according to the invention, said branches are made up of several parts and each branch comprises a stationary part and a movable working part hinged thereto, the working parts of both branches have one common central guide which embraces them, is bent in the direction of their curve, and is rigidly secured on central rods installed on the stationary parts of the branches, a movable rod being placed between said stationary parts of the branches, whose one end is connected with the drive of the diverging device, while the other end carries the diverging device connected to the movable working parts of the branches and made as a slide fitted on the central rods which are guides for the slide.

This provides a capability to dilate the wound edges without interruptions and swiftly to a required size during the operation without inflicting trauma wound edges.

BRIEF DESCRIPTION OF THE ACCOMPANYING DRAWINGS

The invention will now be described in greater detail with reference to a specific embodiment thereof, taken in conjunction with the accompanying drawings, wherein.

DETAILED DESCRIPTION OF THE INVENTION

Figure 1:
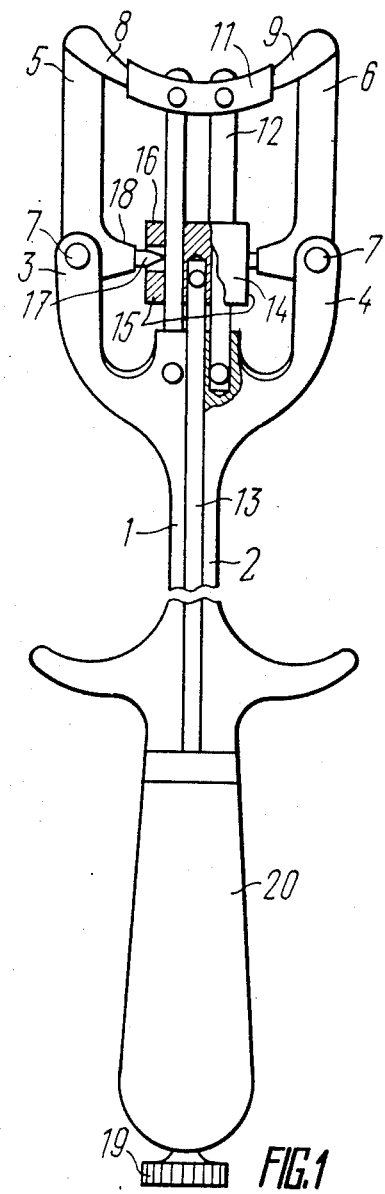
FIG. 1 shows a schematic general view of a surgical wound retractor, according to the invention.
Figure 2:
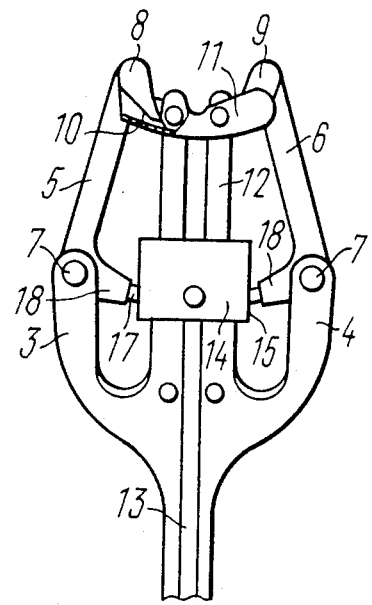
FIG. 2 shows an enlarged view of the working part of the wound retractor, according to the invention.

A surgical wound retractor comprises two diverging branches 1 and 2 (FIG. 1).

Each branch 1 or 2 comprises stationary parts 3 and 4, and movable parts 5 and 6. The stationary parts 3 and 4 are connected by means of hinges 7 to the movable parts 5 and 6 of the branches 1 and 2.

Ends 8 and 9 of the working parts 5 and 6 of the diverging branches 1 and 2 are bent into each other and installed so they can move in a slot 10 of a central quide 11. The central guide 11 is curved as the ends 8 and 9 of the working parts 5 and 6.

The central guide 11 is rigidly secured in central rods 12 connected to the stationary parts 3 and 4 of the branches 1 and 2. A movable rod 13 is positioned between the stationary parts 3 and 4 of the branches 1 and 2. One end of the rod 13 is connected to a slide 14 which is capable of moving along the central rods 12.

Recessions 16 are provided in lateral surfaces 15 of the slide 14 to accomodate hinges 17. The hinges 17 are provided on the lateral projections 18 of the diverging branches 1 and 2.

The other end of the rod 13 culminates in a knob 19 of the drive (not shown) which moves the slide 14 of the diverging device of the branches 1 and 2. This drive is a kinematic pair, for example, a screw pair.

The branches 1 and 2 have a common handle 20.

A surgical wound retractor (FIG. 1) for diverging, for example, the edges of an atrium wound during open-heart operations, such as implantation of artificial heart valves, valvuloplasty, stenosis dilation, etc., operates as follows.

Figure 3:
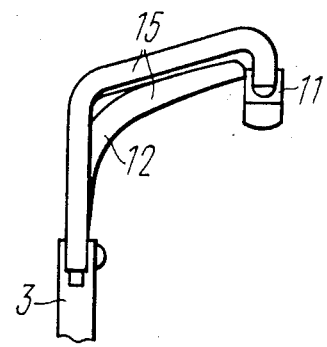
FIG. 3 shows a schematic view of the curved working part of a branch of a wound retractor, according to the invention.

The wound retractor is introduced into an incision made in the atrium wall (not shown) with its working parts 5 and 6 brought together. In this position the ends 8 and 9 of the working parts 5 and 6 of the diverging branches 1 and 2 are completely withdrawn into the recess 10 of the central guide 11. The width of the working parts 5 and 6 introduced into the incision in the atrium wall is minimal. Since the branches 1 and 2 and the central rods 12 with the guide 11 secured thereon are curved as a hook (FIG. 3), the wound retractor can be manipulated as a conventional hook, when introduced into the incision and retracting the edges of the wound. The surgeon can thus take his hand away from the operative field, holding the wound retractor by the handle 20. He has a satisfactory freedom for maneuver, which also improves the conditions for visual control of the operative field. After the working parts 5 and 6 of the diverging branches 1 and 2 of the wound retractor are introduced into the incision in the atrium wall, the knob 19 of the movable rod 13 should be rotated to make the slide 14 move along the central rods 12. The movement of the slide 14 makes the branches 1 and 2 move on the hinges 17. The working parts 5 and 6 of the branches 1 and 2 turn about the hinges 7 installed led in the stationary parts 3 and 4 of the branches 1 and 2 of the wound retractor. The working parts 5 and 6 of the branches 1 and 2 move smoothly and dilate the edges of the atrium wound to a desired size.

In this manner the wound retractor made according to the invention operates ensuring an uninterrupted and swift dilation of an operative wound to a desired size with minimal trauma to the surrounding tissues. This provides convenient conditions for the surgeon who has freedom of maneuvering, satisfactory field of vision of the operative field. The length of the operation is shortened contributing to better results in the postoperative period.

What we claim is:

1. A surgical wound retractor comprising:
   two diverging branches, each having a stationary part and a movable working part made as a hook whose one end is hinged to said stationary part, while the other end is curved in an arc;
   a central guide embracing both said curved ends of said movable working parts of said branches, said central guide being curved in the direction of the curve of the ends of the working parts of said branchs embraced thereby;
   two central rods positioned between said movable parts, one end of each rod is rigidly connected to said central guide, while the other end is rigidly secured to said stationary part of a respective branch;
   a movable rod positioned between and along said central rods and stationary parts of said branches;
   a diverging device including a slide rigidly secured on the end of said movable rod, said slide being installed so that it can move along said central rods which are guides for said slide and connected to said movable working parts of said branches; and
   a drive of said diverging device being rigidly secured to the other end of said movable rod.

2. A surgical wound retractor as claimed in claim 1, wherein said drive of said diverging device is a nut rigidly secured to a screw thread defined by said other end of said movable rod.

* * * * *